(12) United States Patent
Golden et al.

(10) Patent No.: US 6,658,894 B2
(45) Date of Patent: Dec. 9, 2003

(54) PROCESS AND ADSORBENT FOR THE RECOVERY OF KRYPTON AND XENON FROM A GAS OR LIQUID STREAM

(75) Inventors: Timothy Christopher Golden, Allentown, PA (US); Thomas Stephen Farris, Bethlehem, PA (US); Robert Ling Chiang, Basking Ridge, NJ (US); Roger Dean Whitley, Allentown, PA (US); Fred William Taylor, Coplay, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 10/208,078

(22) Filed: Jul. 29, 2002

(65) Prior Publication Data

US 2003/0106335 A1 Jun. 12, 2003

Related U.S. Application Data

(63) Continuation-in-part of application No. 09/992,744, filed on Nov. 19, 2001.

(51) Int. Cl.[7] .................................................. F25J 3/00
(52) U.S. Cl. ......................................................... 62/652
(58) Field of Search ........................... 62/617, 640, 648, 62/643, 652

(56) References Cited

U.S. PATENT DOCUMENTS

| | | | |
|---|---|---|---|
| 3,191,393 A | 6/1965 | Dennis | 62/42 |
| 3,596,471 A | 8/1971 | Streich | 62/20 |
| 3,609,983 A | 10/1971 | Lofredo et al. | 62/22 |
| 3,751,934 A | 8/1973 | Frischbler | 62/41 |
| 3,768,270 A | 10/1973 | Schuftan | 62/31 |
| 3,779,028 A | 12/1973 | Schuftan et al. | 62/22 |
| 3,971,640 A | 7/1976 | Golovko | 55/66 |
| 4,369,048 A | 1/1983 | Pence | 55/66 |
| 4,384,876 A | 5/1983 | Mori et al. | 62/22 |
| 4,401,448 A | 8/1983 | La Clair | 62/22 |
| 4,417,909 A | 11/1983 | Weltmer, Jr. | 62/12 |
| 4,421,536 A | 12/1983 | Mori et al. | 62/18 |
| 4,447,353 A | 5/1984 | Pence et al. | 252/630 |
| 4,568,528 A | 2/1986 | Cheung | 423/262 |
| 4,647,299 A | 3/1987 | Cheung | 62/22 |
| 4,874,592 A | 10/1989 | Shino et al. | 423/262 |
| 5,039,500 A | 8/1991 | Shino et al. | 423/262 |
| 5,067,976 A | 11/1991 | Agrawal et al. | 62/22 |
| 5,122,173 A | 6/1992 | Agrawal et al. | 62/22 |
| 5,309,719 A | 5/1994 | Agrawal et al. | 62/22 |
| 5,313,802 A | 5/1994 | Agrawal et al. | 62/22 |
| 5,784,898 A | 7/1998 | Daniel | |
| 5,833,737 A | 11/1998 | Tamura et al. | 95/98 |
| 6,083,301 A | 7/2000 | Daniel et al. | |

FOREIGN PATENT DOCUMENTS

| | | | |
|---|---|---|---|
| WO | WO 00/40332 | 7/2000 | |
| WO | WO00/40332 | 7/2000 | B01J/20/18 |

*Primary Examiner*—Denise L. Esquivel
*Assistant Examiner*—Malik N. Drake
(74) *Attorney, Agent, or Firm*—Willard Jones, II (57) ABSTRACT

Xenon and/or krypton are recovered from oxygen containing gas, typically derived from liquid oxygen bottoms in a cryogenic air separation plant, by selective adsorption on a Li and Ag exchange zeolite containing 5 to 40% Ag exchange capacity on an equivalents basis, with periodic thermal regeneration of the adsorbent.

35 Claims, 5 Drawing Sheets

Figure 1

Figure 2
Fractional Desorption of Kr and O2 During N2 Purge at -160°C

Figure 3

PROCESS AND ADSORBENT FOR THE RECOVERY OF KRYPTON AND XENON FROM A GAS OR LIQUID STREAM

CROSS REFERENCE TO RELATED APPLICATIONS

This application is a continuation-in-part of that certain application filed with the USPTO on Nov. 19, 2001 and designated U.S. Ser. No. 09/992,744.

STATEMENT REGARDING FEDERALLY SPONSORED RESEARCH

Not applicable.

FIELD OF THE INVENTION

The present invention relates to a process and adsorbent for the recovery of krypton and/or xenon from gas or liquid streams, and to an apparatus for use in an adsorption process.

BACKGROUND OF THE INVENTION

The use of the noble gases krypton and xenon is expected to rise in the coming years. Krypton is primarily used in the global lighting industry, for example in long-life light bulbs and automotive lamps. Xenon has applications in the aerospace, electronics and medical fields. In the aerospace industry, xenon is used in ion propulsion technology for satellites. Xenon provides ten times the thrust of current chemical propellants, is chemically inert and can be stored cryogenically. This results in lower "fuel" weight so that satellites can accommodate more useful equipment. Xenon also finds applications in the medical market as an anaesthetic and in X-ray equipment, and in the electronics market for use in plasma display panels.

Krypton and xenon are produced by concentration from air. Since their concentrations in air are so small (krypton 1.14 ppmv and xenon 0.086 ppmv).large volumes of air must be processed to produce reasonable quantities of krypton and xenon. An issue of interest is the recycling of xenon from the air of operating rooms where it has been used as an anaesthetic.

In practice, krypton and xenon are reclaimed from the liquid oxygen portion of a cryogenic air distillation process. Since the volatilities of krypton and xenon are lower than that of oxygen, krypton and xenon concentrate in the liquid oxygen sump in a conventional air separation unit. This concentrated stream of krypton and xenon can be further concentrated by stripping some oxygen in a distillation column to produce "raw" krypton and xenon. However, this "raw" stream contains other air impurities less volatile than oxygen which have to be removed before pure krypton or xenon can be produced. In particular, the "raw" stream contains carbon dioxide and nitrous oxide, both of which have low solubility in liquid oxygen and tend to freeze out during the concentration of krypton and xenon, resulting in operational problems. In addition, various hydrocarbons ($C_1$ to $C_3$) present in the liquid oxygen can concentrate during the stripping of oxygen to produce a liquid oxygen stream with dangerously high levels of hydrocarbons.

These problems may be addressed by the use of a "guard adsorber", that is, an adsorber capable of adsorbing impurities from the liquid oxygen stream before the oxygen stripping step.

A number of U.S. patents (U.S. Pat. No. 4,568,528, U.S. Pat. No. 4,421,536, U.S. Pat. No. 4,401,448, U.S. Pat. No. 4,647,299, U.S. Pat. No. 5,313,802, U.S. Pat. No. 5,067,976, U.S. Pat. No. 3,191,393, U.S. Pat. No. 5,309,719, U.S. Pat. No. 4,384,876 and U.S. Pat. No. 3,751,934) describe krypton and xenon recovery processes where guard adsorbers are not used. These patents disclose various ways of reducing methane concentration in krypton and xenon by reducing reflux ratios in the raw distillation column.

U.S. Pat. No. 3,779,028 describes an improved method for recovery of krypton and xenon from a reboiler of an air separation unit. The oxygen-rich liquid which leaves the reboiler passes through an adsorber for the removal of acetylene and other hydrocarbons. There is no disclosure of the type of adsorbent used or of the removal of carbon dioxide or nitrous oxide. Oxygen and residual hydrocarbons are removed from the oxygen-rich liquid, for example using a hydrogen blowpipe, and the resulting secondary concentrate of krypton and xenon is vaporised and passed through an adsorbent, for example active charcoal, silica gel or molecular sieve. Separate krypton and xenon fractions may be collected from the adsorbent.

U.S. Pat. No. 3,768,270 describes a process for the production of krypton and xenon. A portion of the liquid oxygen from the reboiler passes through an adsorber for removal of acetylene and carbon dioxide. As in U.S. Pat. No. 3,779,028, the adsorbent used in the adsorber is unspecified and removal of nitrous oxide is not addressed. The oxygen and hydrocarbons that are not removed in the adsorber are subsequently removed by combustion with hydrogen. The resulting concentrate of krypton and xenon is treated as in U.S. Pat. No. 3,779,028.

U.S. Pat. No. 3,609,983 also describes a krypton and xenon recovery system. In this system, a liquid oxygen stream is passed through a pair of alternating guard adsorbers where acetylene and higher hydrocarbons are removed. The stream is then further purified by distillation. The hydrocarbons which are not removed in the guard adsorbers are catalytically combusted, and the resultant carbon dioxide and water are frozen out by heat exchangers. The stream is purified by a final distillation. This document discloses the use of silica gel as a guard bed adsorbent.

U.S. Pat. No. 3,596,471 also describes a krypton and xenon recovery process. The process employs a hydrocarbon adsorber for removal of hydrocarbons from a krypton- and xenon-containing liquid oxygen stream. The stream is then stripped of oxygen by contact with gaseous argon, residual hydrocarbons are burned and the combustion products removed, and the stream is distilled to afford a mixture of krypton and xenon. No disclosure is made of the type of adsorbent used or of carbon dioxide and/or nitrous oxide adsorption.

U.S. Pat. No. 5,122,173 also discloses a process for recovery of krypton and xenon from liquid oxygen streams. The process employs an adsorber for higher hydrocarbons and nitrous oxide, but the adsorbent material is not indicated.

U.S. Pat. No. 4,417,909 describes a process for recovering krypton and xenon from the off-gas stream produced during nuclear fuel reprocessing. Water and carbon dioxide are removed by adsorption at ambient temperature and at −100° F. respectively, using molecular sieves. The water and carbon dioxide free stream is then passed through a bed of silica gel which removes essentially all of the xenon from the stream. The xenon is then recovered from regeneration effluent of the silica gel bed by freezing out in a liquid nitrogen cooled metal container. This art teaches selective xenon adsorption on silica gel.

U.S. Pat. No. 3,971,640 describes a low temperatures adsorptive process for the separation of krypton and xenon from a nitrogen-rich stream. The separation is carried out in an oxygen-lean stream to minimise the potential of explosions between oxygen and hydrocarbons. The krypton- and xenon-containing stream at 90 to 100 K is sent through a first adsorbent bed of silica gel to adsorb xenon, krypton and nitrogen. The effluent from the first bed is then sent to another bed which contains synthetic zeolite. Krypton, nitrogen, oxygen and hydrocarbons are adsorbed on the second adsorbent. Alternatively, the gases are adsorbed on one adsorbent only. The adsorbed gases are then desorbed by stepwise heating from 105 to 280 K, then to 650 K. This document thus teaches the use of silica gel as an adsorbent for xenon. No guard adsorbent is disclosed.

U.S. Pat. No. 4,874,592 also describes an adsorptive process for the production of xenon. As in U.S. Pat. No. 3,971,640, silica gel (or active carbon or zeolite) is used as a selective xenon adsorption agent. The concentrated xenon so obtained is purified by catalytic removal of hydrocarbons.

U.S. Pat. No. 5,833,737 describes an ambient temperature pressure swing adsorption process for the recovery of krypton from air. The key to the process is the use of hydrogen mordenite as the adsorbent selective for krypton.

U.S. Pat. No. 5,039,500 describes an adsorptive xenon recovery process which uses an adsorbent such as silica gel to selectively adsorb xenon and krypton from a liquid oxygen stream. The concentrated krypton and xenon stream is desorbed by heating and evacuation. The desorbed stream is then admitted to a low temperature solid-gas separating column to solidify and capture the xenon. No guard adsorbent is used in this process.

U.S. Pat. No. 4,369,048 and U.S. Pat. No. 4,447,353 teach methods for treating gaseous effluents from nuclear reactors. Radioactive krypton and xenon produced during nuclear fission must be captured and stored. In these documents, radioactive xenon is adsorbed at ambient temperature on a silver exchanged zeolite, while radioactive krypton is adsorbed on the same type of zeolite at lower temperature, about −140° C. Water and carbon dioxide are pre-adsorbed on zeolite molecular sieves, and nitrogen oxides are also pre-adsorbed. All steps in their processes, with the exception of krypton adsorption, are carried out at near atmospheric temperature and pressure.

U.S. Pat. No. 5,039,500 discloses an adsorption process for the recovery of xenon from oxygen streams. The adsorbent used is silica gel. Xenon is collected by freezing out.

WO00/40332 discloses the use of Li and Ag exchanged X type zeolites for separating nitrogen from oxygen and comments that Li exchanged zeolites are somewhat selective for oxygen as compared to argon, whereas Ag exchanged zeolites showed no selectivity for oxygen over argon. It is said that Li Ag exchanged zeolites are adaptable for selectivity for oxygen over argon, although the degree of selectivity demonstrated is very small, and that Ag ions adsorb nitrogen strongly.

BRIEF SUMMARY OF THE INVENTION

In a first aspect, the present invention provides a process for recovering xenon and/or krypton from an oxygen containing gas stream also containing xenon and/or krypton inert gas comprising selectively adsorbing the inert gas on a solid adsorbent and desorbing and collecting the adsorbed inert gas, wherein the adsorbent is a Li and Ag exchanged X type zeolite.

The term X type zeolite is used herein to embrace low silica X type zeolites. Typical X type zeolite may have an Si/Al ratio of 1.25 but low silica X type zeolites as known in the art may have a lower Si/Al ratio, e.g. 1.0–1.05. Thus the use of X type zeolites with Si:Al ratio's of 1.0 to 1.5 at least is included within the invention.

Preferably, the adsorbent comprises silver and lithium exchanged X zeolite with a silver exchange level of 5 to 40% equivalents, for example about 20%. As is conventional, the silver exchange level as a percentage on an equivalent basis is given by:

$$\frac{\text{Exchange capacity of zeolite Ag}^+ \text{ in equivalents}}{\text{Total exchange capacity of zeolite in equivalents}}$$

Preferably, the zeolite has a silicon to aluminium ratio of 1.0 to 2.5.

Preferably, the gas stream has a temperature of 90 to 303 K (more preferably 90 to 110 K) as it is passed in contact with the adsorbent. Preferably, the zeolite has a temperature of 120 to 398 K (more preferably 120 to 298 K) during desorption of the inert gas. Preferably, the gas stream has a pressure of 5 to 150 psig (34.4–1034 kPa) as it is passed in contact with the adsorbent.

Preferably, the second adsorbent has a particle size of 0.5 to 2.0 mm.

Preferably, oxygen is desorbed from the zeolite before the inert gas is desorbed from the zeolite. Preferably, oxygen is desorbed from the zeolite by a flow of oxygen-displacing gas. Preferably, the oxygen-displacing gas is an unreactive gas, more preferably the oxygen-displacing gas comprises one or more gases selected from the group consisting of nitrogen, argon and helium. In a preferred embodiment, the oxygen-displacing gas is cold nitrogen. The preferred temperature of the oxygen-displacing gas is 90 to 173 K. The preferred pressure of the oxygen-displacing gas is 5 to 150 psig (34.4 to 1034 kPa). The flow of oxygen-displacing gas is preferably co-current to the oxygen-containing gas stream flow.

The inert gas may then be desorbed from the zeolite by evacuation, purging, and/or thermal regeneration following the oxygen-displacing step.

The krypton and/or xenon may be desorbed from the zeolite by purging with a desorption gas. Preferred desorption gases comprise nitrogen, argon, helium, hydrogen or a mixture of two or more thereof. Preferably, the adsorbent has a temperature of 120 to 373 K during desorption of krypton and/or xenon. Preferably, the krypton and/or xenon is desorbed with a flow of desorption gas counter-current to the oxygen-containing gas stream (feed) flow. The preferred desorption pressure is 0.2 barg to 5 barg (5.1 to 128.3 kPa).

The krypton and/or xenon are recovered in a product gas stream and are suitably removed therefrom by freezing out. Alternatively, the product gas stream may be distilled to obtain pure krypton and/or xenon.

Thermal desorption may involve active heating, for example by heated rods or coils in the adsorption vessel or by external heating. Such active heating reduces the amount of required desorption flow to maximise the concentration of inert gas in the product stream.

Xenon is finding increasing use as an anaesthetic gas and as a neuroprotectant, but it is much more expensive than nitrous oxide and it is therefore highly desirable that it be recovered and recycled for future use. When the anaesthetic is exhaled by a patient it is naturally mixed with oxygen, nitrogen, carbon dioxide and water and also hydrocarbons derived from the equipment. In one preferred process according to the invention as described above, xenon is recovered from an oxygen and nitrogen mixture containing xenon at a concentration higher than that of xenon in atmospheric air, for instance in a process in which xenon is recovered from a mixture chiefly comprising oxygen and nitrogen, being or derived from exhaled gas or blood from a patient anaesthetised or neuroprotected using xenon. This is possible because although the silver and lithium exchanged zeolite has been used for separating nitrogen (more strongly adsorbed) from oxygen (less strongly adsorbed), xenon is more strongly adsorbed than nitrogen on this adsorbent. This is in contrast to argon, which is adsorbed similarly to oxygen, as discussed above.

We have found that the Henry's Law constants (initial isotherm slope) at 303 K for relevant gases on these adsorbents is as shown in the following table:

| Gas | Henry's Law constant mmole/g/atm |
|---|---|
| Oxygen | 0.19 |
| Nitrogen | 3.8 |
| Xenon | 73.9 |
| Krypton | 4.9 |

Thus, when the adsorbent bed is exposed to a flow of a mixture of these four gases, nitrogen is initially adsorbed in preference to oxygen, but is eventually displaced from the bed by both krypton and xenon.

Alternatively, the invention may be employed in a process for recovering xenon and/or krypton from liquid oxygen containing xenon and/or krypton comprising vaporising the liquid oxygen to form a gas stream and recovering xenon and/or krypton therefrom by a process as described above.

More generally, the invention may be used in a process for recovering krypton and/or xenon from a liquefied gas stream containing one or more of krypton and xenon and one or more of carbon dioxide, nitrous oxide and hydrocarbon impurities, the process comprising:

passing the liquefied gas stream in contact with a first adsorbent capable of removing one or more impurities from the gas stream;

vaporising the liquefied gas stream to form a gas stream;

passing the gas stream in contact with a second adsorbent capable of removing krypton and/or xenon from the gas stream;

periodically desorbing krypton and/or xenon from the second adsorbent to form a product gas stream; and periodically regenerating the first adsorbent, wherein the second adsorbent is a Li and Ag exchanged X type zeolite.

Preferably, the liquefied gas stream is an oxygen-rich liquefied gas stream, for example an oxygen-rich liquefied gas stream obtained by fractional distillation of air.

Preferably, the first adsorbent is silica gel. More preferably, the silica gel has a surface area of at least 650 $m^2/g$. Preferably, the silica gel particle size is from 0.5 to 2 mm.

Preferably, the liquefied gas stream has a temperature from 90 to 110 K as it is passed in contact with the first adsorbent. Preferably, the liquefied gas stream has a pressure of 0 to 150 psig (0 to 1034 kPa) as it is passed in contact with the first adsorbent.

Preferably, the liquefied gas stream is vaporised at a temperature of 120 to 303 K.

The conditions for the recovery of the xenon and/or krypton from the gaseous stream are as described above in accordance with the first aspect of the invention.

In accordance with all aspects of the invention, typically, at least two beds of the inert gas adsorbent are used, such that the gas stream is passed in contact with a first bed of adsorbent whilst krypton and/or xenon and optionally oxygen are desorbed from a second bed of the adsorbent. The gas stream is then passed in contact with the second bed of the adsorbent whilst krypton and/or xenon and optionally oxygen are desorbed from the first bed of adsorbent. Waste gas from the gas stream after passing in contact with the first bed of adsorbent may be used for final purge and repressurisation of the second bed of adsorbent, and vice versa.

In embodiments where a guard bed is used typically at least two beds of the guard bed (first) adsorbent are used, such that the liquefied gas stream is passed in contact with a first bed of first adsorbent whilst a second bed of first adsorbent is regenerated. The liquefied gas stream is then passed in contact with the second bed of first adsorbent whilst the first bed of first adsorbent is regenerated. Regeneration may be carried out by evacuation or purging, but is preferably carried out thermally (thermal swing adsorption process), for example at a temperature of 298 to 423 K.

Regeneration of the guard bed is preferably carried out with a gas stream essentially free of the impurities adsorbed by the guard bed, e.g. a stream of nitrogen. Preferably, the gas stream flow is counter-current to the oxygen containing gas stream.

Alternatively, the system could comprise one set of adsorber beds. In this case, when the beds are being regenerated, the feed liquid is collected in a holding tank.

Once the beds have been regenerated, the collected liquid is then sent to the adsorbers. This system is desirable since it reduces cost by reducing the number of vessels and number of valves.

Additionally, the system could comprise only one adsorber bed. In this embodiment, a vaporized oxygen-rich stream is sent to an adsorber vessel that contains the guard adsorbent (silica gel or zeolites, like CaX) and the rare gas recovery adsorbent (AgLiX). In this case, feed liquid is collected in a holding tank during regeneration of the adsorbent. The desorbed product gas contains carbon dioxide and nitrous oxide which must be removed during further processing of the rare gas-enriched stream.

In a third aspect, the present invention relates to a process comprising adsorption of krypton and/or xenon on an adsorbent comprising silver and lithium exchanged X zeolite. Preferably, the process further comprises desorption of krypton and/or xenon from the adsorbent.

In a fourth aspect, the present invention relates to an apparatus for carrying out a process of adsorption and collection of a component of a feed gas, comprising:

a first adsorbent bed;

a second adsorbent bed downstream of the first adsorbent bed;

an upstream manifold positioned upstream of the first adsorbent bed;

an intermediate manifold positioned between the first and second adsorbent beds;

a downstream manifold positioned downstream of the second adsorbent bed;

a first inlet in the upstream manifold to control the flow of a feed gas across the first and second adsorbent beds;

a second inlet in the intermediate manifold to control the counter-current flow of a first regeneration gas across the first adsorbent bed only;

a third inlet in the intermediate manifold to control the co-current flow of a second regeneration gas across the second adsorbent bed only; and a fourth inlet in the downstream manifold to control the counter-current flow of a desorption gas across the second adsorbent bed only.

Preferably, the downstream manifold contains a first exhaust outlet for feed gas and a second exhaust outlet for second regeneration gas. Preferably, the intermediate manifold contains a third exhaust outlet for desorption gas. Preferably, the upstream manifold contains a fourth exhaust outlet for first regeneration gas.

Optionally, the apparatus further comprises an accumulation vessel upstream of the upstream manifold for the accumulation of liquefied feed during passing of the first and second regeneration gases and the desorption gas across the adsorbent beds. This enables a single guard bed and krypton/xenon adsorbent bed to be used for krypton/xenon recovery without interrupting the flow of feed gas.

Optionally, an additional first adsorbent bed and an additional second adsorbent bed are connected to the upstream manifold, intermediate manifold and downstream manifold of the apparatus such that feed gas is passed across one first and second adsorbent bed while first and second regeneration gases and desorption gas are passed across the other first and second adsorbent bed, with periodic changes. This allows continuous krypton/xenon recovery with no need to accumulate feed gas whilst regeneration and desorption occur.

BRIEF DESCRIPTION OF THE DRAWINGS

The invention will be further described and illustrated with reference to the accompanying drawings, in which.

DETAILED DESCRIPTION OF PREFERRED EMBODIMENTS OF THE INVENTION

Figure 1:
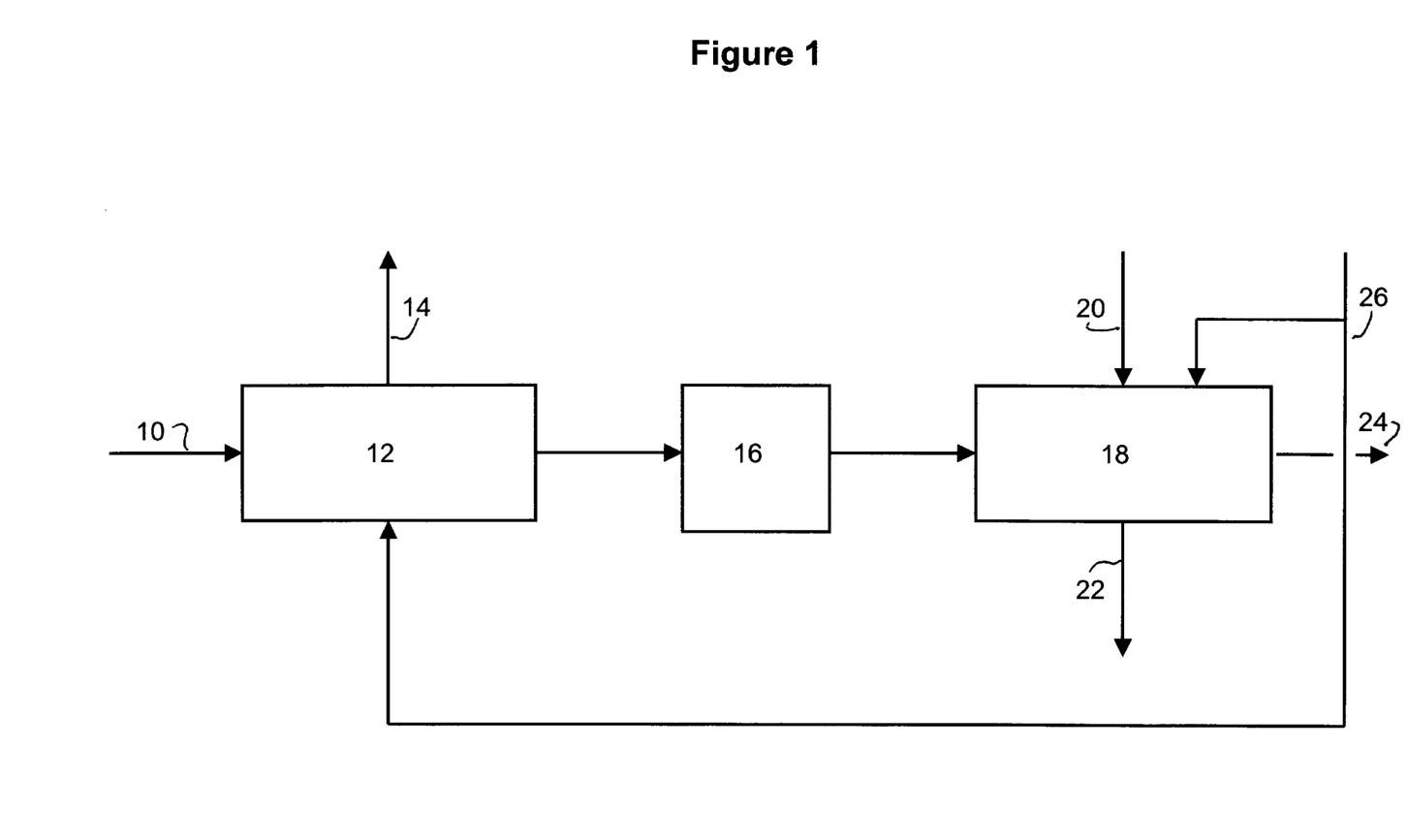
FIG. 1 shows a schematic diagram of the process of a preferred embodiment of the invention.

According to a preferred practice of the invention schematically illustrated in FIG. 1, a cryogenic distillation of air produces a liquid oxygen stream 10 enriched in xenon and krypton with respect to atmospheric air concentrations, and suitably containing xenon at a concentration of 20–60 ppm. The liquid oxygen also contains $CO_2$ and $N_2O$, and various hydrocarbons chiefly in the $C_1$–$C_4$ range as impurities.

Using a dual bed system, the liquid oxygen is passed over a guard bed 12 of silica gel as described above, whilst a second bed of silica gel is thermally regenerated by a flow of nitrogen or waste gas from the inert gas adsorption process, producing an impurity stream 14. The $CO_2$ and $N_2O$ are adsorbed together with the higher hydrocarbons, but some methane and ethane will generally pass through. The removal of olefins is necessary because they would adsorb strongly on the LiAgX adsorbent used in the next step.

The liquid oxygen stream after purification by the guard bed is vaporised to form a gas stream at 16. In a second dual bed adsorber 18, the gaseous stream is contacted with a bed of LiAgX adsorbent under the conditions described above. Some oxygen 24 passes through and some oxygen and xenon and krypton are adsorbed and recovered during bed regeneration. Preferably oxygen is displaced by a co-current flow of cold nitrogen, following which krypton and xenon are collected by thermal regeneration and counter-current purging with hot nitrogen 20, thus avoiding potentially explosive concentrations of hydrocarbons and oxygen in the desorbed gas 22. Desorption of oxygen and inert gas at opposite ends of the LiAgX bed allows the inert gas to be recovered with minimum oxygen contamination. A surprising finding underlying this aspect of the invention is that it is possible, using for instance a nitrogen purge, to displace essentially all of the oxygen from the bed in a co-current purge step, without desorbing any of the adsorbed inert gas. This renders the adsorbed inert gas inherently safe by making it oxygen free. It can then be recovered in the preferably counter-current regeneration of the bed. Final purge and repressurisation of the inert gas selective beds is carried out with waste gas 26 from the other inert gas adsorber or with $N_2$. Alternatively, xenon and krypton are recovered as solids in a liquid nitrogen cooled receiving tank.

The invention may be operated with a single bed system wherein vaporised liquid oxygen is fed directly to the LiAgX adsorbent. In this system, carbon dioxide, nitrous oxide and hydrocarbons will remain in the krypton/xenon enriched product, but can be removed in downstream processing. In this case, it is possible to use a pre-layer (at the feed end of the bed) of adsorbent selective for carbon dioxide, nitrous oxide and olefins. Typical adsorbents include silica gel and zeolites, particularly CaX.

The invention will be further described and illustrated with reference to the following examples.

EXAMPLE 1

Adsorption isotherms for oxygen and xenon were measured at 30° C. on silica gel, 13X and 20% AgLiLSX. The results are presented in Table 1, giving the Henry's Law constants (initial isotherm slopes) for krypton, xenon and oxygen. The table also gives the selectivity for xenon over oxygen given in terms of the ratio of their Henry's Law constants. The silica is Grace Davison grade 40 (750 m$^2$/g), 13X is APG grade from UOP and 20% AgLiLSX was produced exchanging silver (I) ions into a commercially available LiLSX.

TABLE 1

| Adsorbent | $K_HO_2$ (mmol/g/atm) | $K_HKr$ (mmol/g/atm) | $K_HXe$ (mmol/g/atm) | Selectivity Xe/$O_2$ |
|---|---|---|---|---|
| Davison Grade 40 silica gel | 0.050 | — | 0.52 | 10.4 |
| UOP 13X APG | 0.073 | 0.26 | 1.2 | 16.4 |
| 20% AgLiLSX | 0.19 | 4.9 | 73.9 | 389 |

The results in Table 1 show that the introduction of silver (I) ions into the zeolite 15 structure greatly enhances the capacity for krypton (19 times greater than 13X) and xenon (62 times greater than 13X). The table also shows that the Ag exchanged zeolite has a surprisingly high xenon/oxygen selectivity. Finally, the selectivity and capacity of the silver exchanged zeolite is much higher than for silica gel, which is the primary adsorbent used in, the prior art for xenon recovery.

EXAMPLE 2

The cryogenic adsorption of xenon from liquid argon (LAR) was measured on silica gel (Grace Davison B-411) and 40% AgLiLSX. Liquid argon with 20 ppm xenon was fed to an adsorber 2 inches in diameter by 20 inches in length until complete breakthrough of xenon was noted. Liquid argon was used as the cryogen because of safety considerations using liquid oxygen (LOX) and it is expected that performance in LAR and LOX should be essentially the same. The flow rate into the adsorber was about 200 lbmoles/ft$^2$/hr (53.4 kgmoles/m$^2$/sec). The results of the breakthrough testing are given in Table 2.

TABLE 2

| Adsorbent | Relative Xe capacity at 20 ppm inlet (mmol/g) |
| --- | --- |
| silica gel | 1.0 |
| 20% AgLiLSX | 21.2 |

The results in Table 2 show that 20% AgLiLSX is a much improved adsorbent over silica gel, the prior art adsorbent, for the selective adsorption of xenon from cryogenic liquids.

EXAMPLE 3

The xenon capacity of 20% AgLiLSX was determined by measuring breakthrough curves at −78° C. (195 K) and −160° C. (113 K) with 20 ppm xenon in argon at a feed pressure of 50 psig (345 kPa). The column used was 5 cm in length and ⅜ inch (32 mm) in diameter. Results of the testing compared with the results obtained in Example 2 are shown in Table 3.

TABLE 3

| Adsorbent | Feed Temperature (K) | Relative Xe Capacity |
| --- | --- | --- |
| 20% AgLILSX | 90 | 1.0 |
| 20% AgLILSX | 113 | 28.5 |
| 20% AgLILSX | 195 | 12.2 |

The results in Table 3 are unexpected since the absorption capacity of Xe goes through a maximum with temperature. This result also indicates that it is preferable to carry out noble gas recovery in the vapour phase.

EXAMPLE 4

Figure 2:
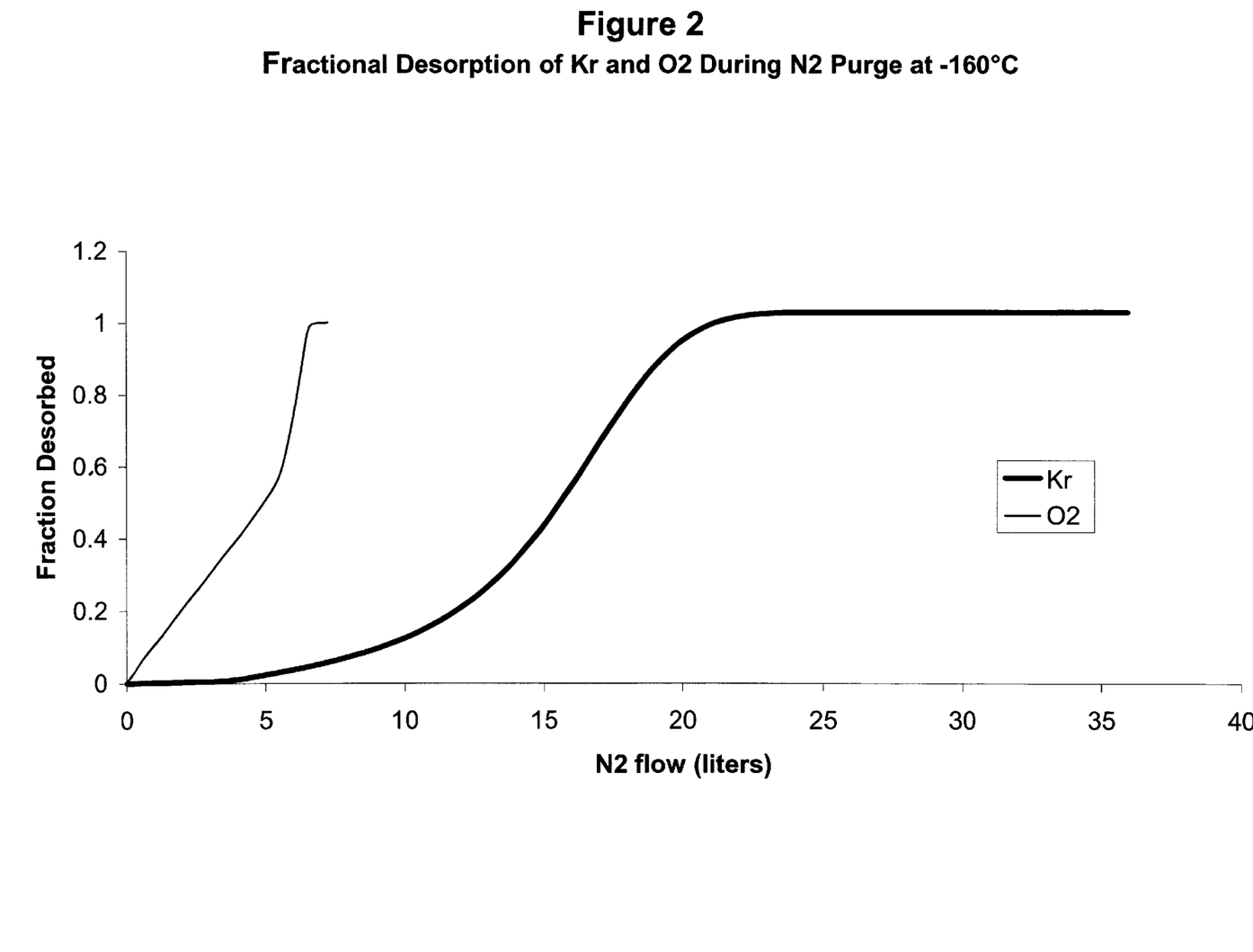
FIG. 2 shows a plot of oxygen and krypton desorption from a bed of 20% AgLiLSX during nitrogen purge at low temperature.

Another key aspect of this invention is to ensure high recovery of krypton and xenon in a safe manner. The principal safety concern is that hydrocarbons and oxygen are present in the adsorption system at the same time. Hence, it is imperative to avoid explosion concentrations during adsorptive processing. The present example avoids explosive concentrations by purging in inert gas such as nitrogen. Prior to desorption in nitrogen at −160° C., the bed was subjected to breakthrough of 80 ppm krypton in oxygen at −160° C. The desorption plot (FIG. 2) shows that the cold nitrogen purge displaces essentially all the oxygen before krypton is desorbed. Thus, product collection does not start until essentially all the oxygen is desorbed from the bed. This process is, therefore, inherently safe, ensures high noble gas recovery and maximises concentration of noble gas by not taking any adsorbed oxygen into the product. The product gas is safe for handling, distilling and transporting.

EXAMPLE 5

Figure 3:
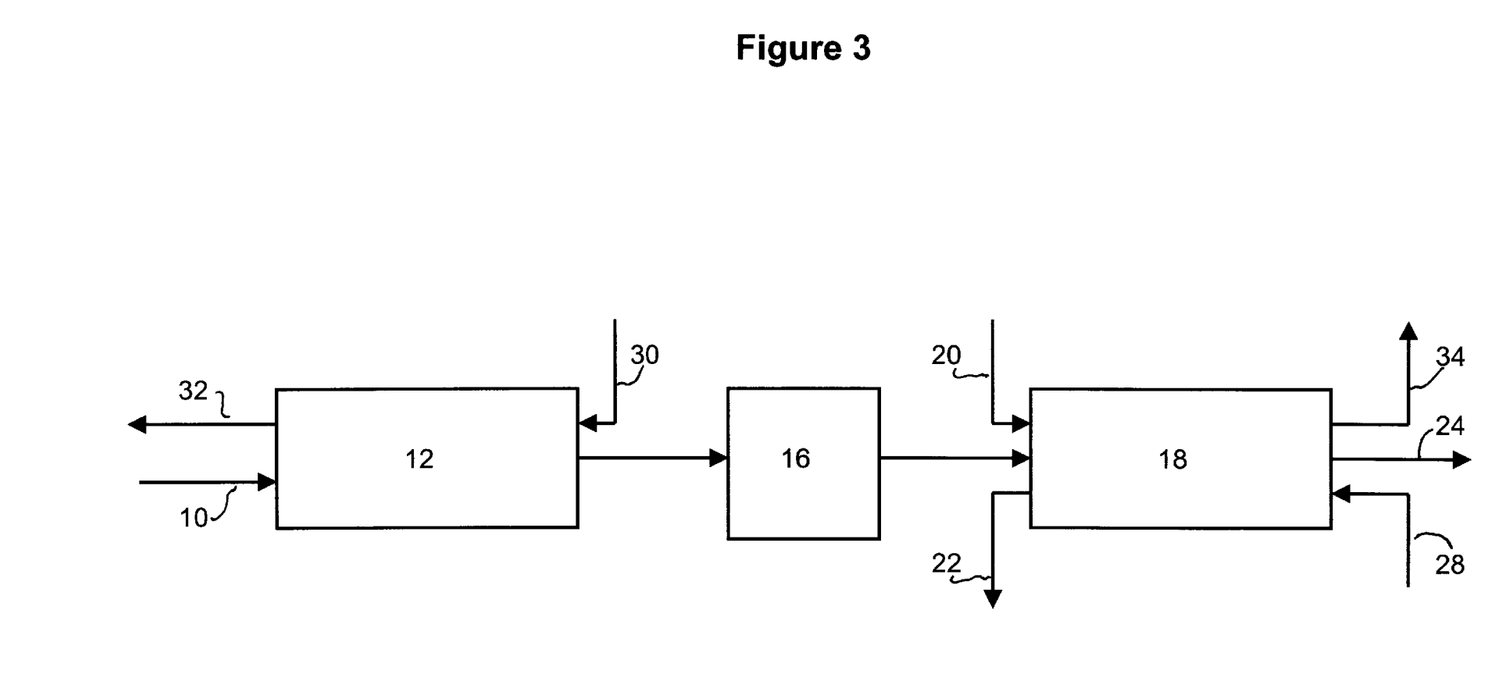
FIG. 3 shows the apparatus of a preferred embodiment of the invention.

The apparatus of a preferred embodiment of the invention is shown in FIG. 3. The apparatus comprises a guard adsorber 12, with a liquid oxygen inlet 10 and a waste outlet 32 upstream, and a product outlet 16 and hot nitrogen inlet 30 downstream. The product outlet 16 is connected to the upstream end of a second adsorbent bed 18. The second adsorbent bed 18 also has a cold nitrogen inlet 20 and krypton/xenon product outlet 22 upstream, and an oxygen outlet 24, waste outlet 34 and hot nitrogen inlet 28 downstream.

A dual bed-system with two parallel guard adsorbers 12 and two parallel second adsorbent beds 18 is used. One guard adsorber 12 and one second adsorbent bed 18 are regenerated while the other guard adsorber 12 and second adsorbent bed are online, with a regular change between beds.

The apparatus is used as is the apparatus of FIG. 1, except that regeneration of the second adsorbent bed 18 is carried out in two stages. First, a co-current cold nitrogen stream at 90 to 173 K is introduced at the upstream inlet 20 such that oxygen is desorbed and leaves the bed via downstream outlet 24. Second, a hot counter-current nitrogen stream at 120 to 373 K enters the bed 18 via downstream inlet 28 such that krypton and xenon are desorbed and leave the bed via upstream outlet 22.

EXAMPLE 6

A silver mordenite was prepared following the instructions in U.S. Pat. No. 4,447,353. The material contained about 19 wt % silver. The adsorption properties of the silver mordenite were then compared with those of 20% AgLiLSX. The Henry's Law constant for the silver mordenite was 30 mmol/g/atm, while that for 20% AgLiLSX was 73 mmol/g/atm. These data clearly show that the xenon capacity of the AgLiLSX material is greater than that for silver mordenite. In addition, the silver loading of the AgLiLSX was about 13 wt %. Therefore, the AgLiLSX material has improved adsorption properties at lower silver loading.

EXAMPLE 7

Figure 4:
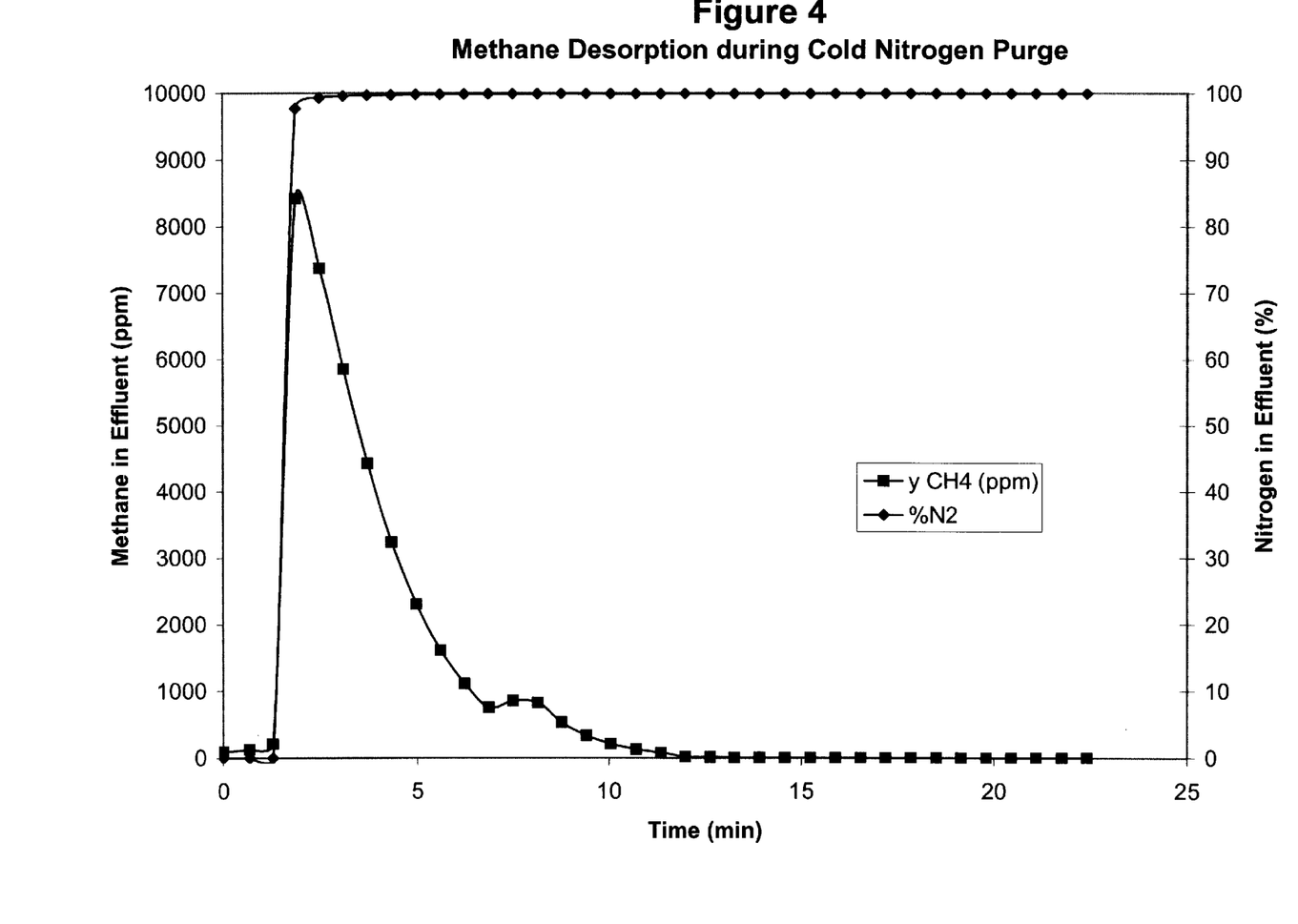
FIG. 4 shows a plot of xenon desorption as temperature is increased.
Figure 5:
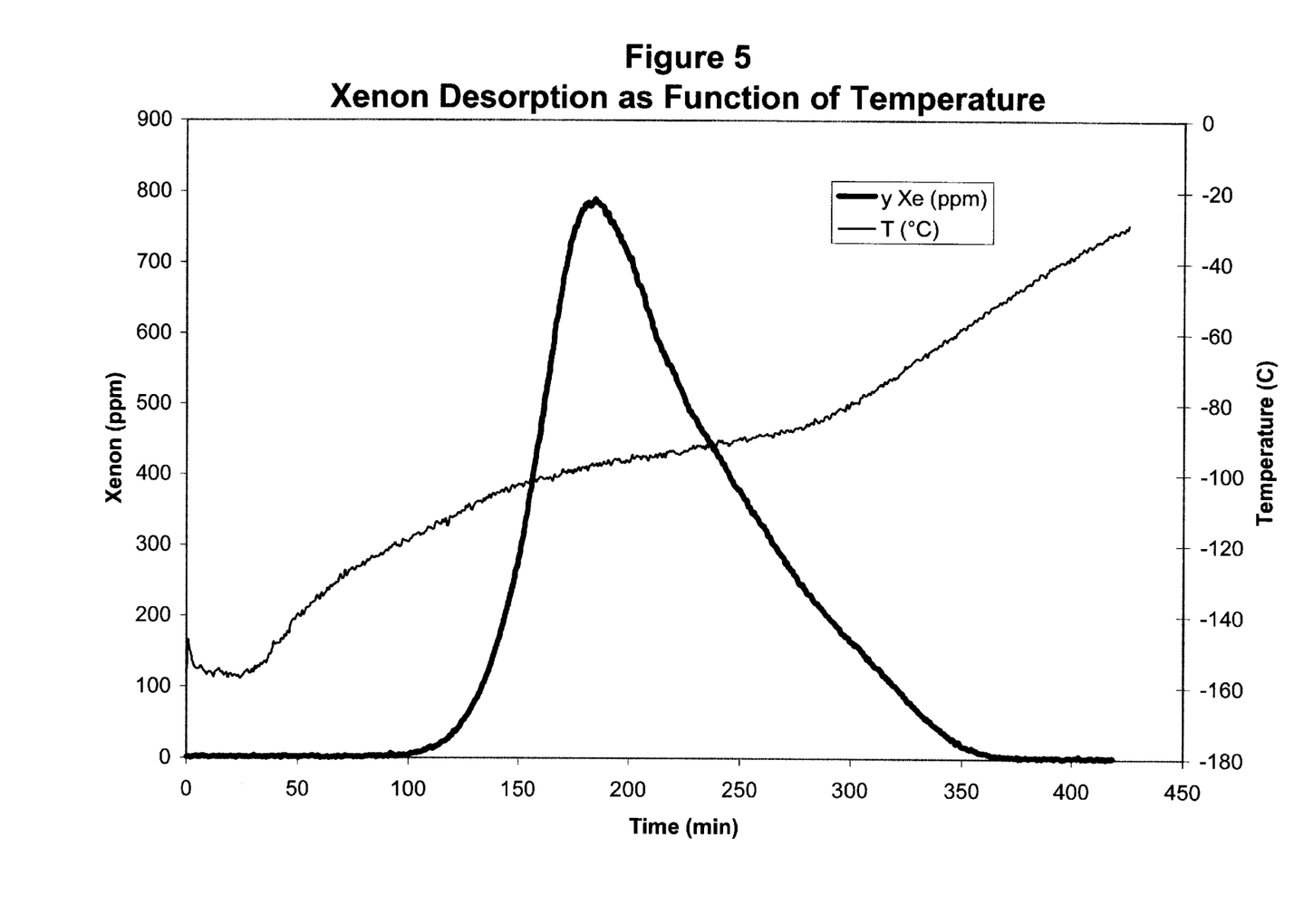
FIG. 5 shows a plot of methane desorption during cold nitrogen purge.

A liquid oxygen stream containing 17 ppm xenon, 95 ppm methane and 10 ppm nitrous oxide was passed through a bed of silica gel (Grace Davison Grade B127) at 90 K and 3 psig. The feed flow rate was 50 lbmoles/hr/ft$^2$ (1 liter liquid/min). The bed size was 2 inches diameter by 18 inches long. Breakthrough of methane and xenon occurred at 3 minutes and 8 minutes respectively. Breakthrough of nitrous oxide occurred at 23.5 hours. The nitrous oxide-free effluent stream from the silica gel bed was vaporized to 113 K and 14 psig. Some of the vaporized stream was sent to a bed containing 20% AgLiX. The bed size was 0.4 inches in diameter by 2 inches long and the feed flow-rate was 6.8 lbmoles/hr/ft$^2$ (1 liter/min). The breakthrough of methane occurred after 190 minutes on feed. After 1400 minutes on feed, breakthrough of xenon had not occurred. The feed step was stopped at 1400 minutes and a co-current nitrogen purge was started 113 K at a G-rate of 3.4 lbmoles/hr/ft$^2$ (0.5 liter/min). During the cold nitrogen purge, which lasted 25 minutes, methane was desorbed to below detectable limits while no xenon desorption occurred (FIG. 4). The nitrogen flow was then heated and passed over the bed in counter-current fashion. Xenon started desorption at 150 K and xenon desorption ended at 220 K (FIG. 5).

The preferred embodiment of the invention illustrated in the Examples provides an economical and safe system for the recovery of krypton and xenon from air separation plants. The gas recovered is free from carbon dioxide, nitrous oxide, hydrocarbons and oxygen.

This embodiment of the invention has a number of particularly surprising features. Firstly, silica gel may be used as a guard adsorbent for carbon dioxide, nitrous oxide and hydrocarbons without adsorbing large quantities of krypton or xenon. This is in contrast to a number of previous processes (for example those of U.S. Pat. No. 4,417,909, U.S. Pat. No. 3,971,640 and U.S. Pat. No. 4,874,592) which rely on silica gel as an adsorbent for xenon and/or krypton. Further, the prior art does not disclose the use of silica gel as an adsorbent for nitrous oxide.

Secondly, the new krypton and xenon adsorbent of the invention AgLiLSX shows high capacity and selectivity for these gases, which are increased at higher feed temperature, as shown in Table 3. By contrast, capacity and selectivity of an adsorbent are usually decreased at high temperature. In the process of the preferred embodiment of the invention, the gas stream is passed in contact with the guard adsorbent in a liquefied state, and is then vaporised before being passed in contact with the noble gas selective adsorbent. This is in contrast with a number of the previous processes disclosed above. For example, in the process of U.S. Pat. No. 4,417,909 the gas stream is gaseous as it is passed in contact with the first and second adsorbents, and in the process of U.S. Pat. No. 3,917,640 the gas stream is in a liquefied state as it is passed in contact with the first and second adsorbents.

Thirdly, the process of the preferred embodiment does not involve refluxing the liquid oxygen mixture before krypton and xenon adsorption. This is in contrast to the processes of U.S. Pat. No. 3,779,028 and U.S. Pat. No. 3,609,983.

We claim:

1. A process for recovering at least one inert gas selected from the group consisting of xenon and krypton from an oxygen-containing gas stream also containing said inert gas comprising selectively adsorbing the inert gas on a solid adsorbent and desorbing and collecting the adsorbed inert gas, wherein the adsorbent is a Li and Ag exchanged X type zeolite.

2. A process as claimed in claim 1, wherein the Ag exchange level of the zeolite is from 5 to 40% on an equivalents basis.

3. A process as claimed in claim 2, wherein the Ag exchange level of the zeolite is about 20%.

4. A process as claimed in claim 1, wherein the zeolite has a silicon to aluminium ratio of 1.0 to 2.5.

5. A process claimed in claim 1, wherein the solid absorbent has an average particle size of 0.5 to 2 mm.

6. A process as claimed in claim 1, wherein the zeolite has a temperature of 120 to 398 K during desorption of the inert gas.

7. A process as claimed in claim 1, wherein the zeolite has a temperature of 90 to 303 K during feed of the gas stream.

8. A process as claimed in claim 1, wherein inert gas is desorbed from the zeolite by evacuation, purging, and/or thermal regeneration.

9. A process as claimed in claim 8, wherein inert gas is desorbed from the zeolite by purging with a flow of regenerating gas counter-current to the oxygen containing gas stream.

10. A process as claimed in claim 8, wherein said inert gas is desorbed from the zeolite by purging with nitrogen, argon, helium, hydrogen or a mixture of two or more thereof.

11. A process as claimed in claim 8, wherein said inert gas is recovered in a product gas stream and is removed therefrom by freezing out.

12. A process as claimed in claim 8, wherein said inert gas is recovered in a product gas stream which is distilled to obtain pure krypton and pure xenon.

13. A process as claimed in claim 1, wherein oxygen is desorbed from the zeolite before said inert gas is desorbed from the zeolite.

14. A process as claimed in claim 13, wherein oxygen is desorbed from the zeolite by purging with a flow of regenerating gas co-current to the oxygen containing gas stream.

15. A process as claimed in claim 1, wherein xenon is recovered from an oxygen and nitrogen mixture containing xenon at a concentration higher than that of xenon in atmospheric air.

16. A process as claimed in claim 12, wherein xenon is recovered from a mixture chiefly comprising oxygen, nitrogen, being or derived from exhaled gas or blood from a patient anaesthetised or neuroprotected using xenon.

17. A process for recovering at least one inert gas selected from the group consisting of xenon and krypton from liquid oxygen containing said inert gas, comprising vaporising the liquid oxygen to form a gas stream and recovering inert gas therefrom by a process as claimed in claim 1.

18. A process for recovering at least one inert gas selected from the group consisting of krypton and xenon from a liquefied gas stream containing said inert gas and one or more of carbon dioxide, nitrous oxide and hydrocarbon impurities, the process comprising:

passing the liquefied gas stream in contact with a first adsorbent capable of removing one or more said impurities from the gas stream;

vaporising the liquefied gas stream to form a gas stream;

passing the gas stream in contact with a second adsorbent capable of removing said inert gas from the gas stream;

periodically desorbing krypton and/or xenon from the second adsorbent to form a product gas stream; and periodically regenerating the first adsorbent, wherein the second adsorbent is a Li and Ag exchanged X-type zeolite.

19. A process as claimed in claim 18, wherein the liquefied gas stream is an oxygen-rich liquefied gas stream.

20. A process as claimed in claim 19, wherein the oxygen-rich liquefied gas stream is obtained by fractional distillation of air.

21. A process as claimed in claim 18, wherein the first adsorbent is silica gel.

22. A process as claimed in claim 21, wherein the silica gel has a surface area of at least 650 $m^2/g$.

23. A process as claimed in claim 21, wherein the silica gel particle size is from 0.5 to 2 mm.

24. A process as claimed in claim 18, wherein the liquefied gas stream has a temperature from 90 to 110 K as it is passed in contact with the first adsorbent.

25. A process as claimed in claim 18, wherein the liquefied gas stream has a pressure of 0 to 150 psig as it is passed in contact with the first adsorbent.

26. An apparatus for carrying out a process of adsorption and collection of a component of a feed gas, comprising:

a first adsorbent bed;

a second adsorbent bed downstream of the first adsorbent bed;

an upstream manifold positioned upstream of the first adsorbent bed;

an intermediate manifold positioned between the first and second adsorbent beds;

a downstream manifold positioned downstream of the second adsorbent bed;

a first inlet in the upstream manifold to control the flow of a feed gas across the first and second adsorbent beds;

a second inlet in the intermediate manifold to control the counter-current flow of a first regeneration gas across the first adsorbent bed only;

a third inlet in the intermediate manifold to control the co-current flow of a second regeneration gas across the second adsorbent bed only; and a fourth inlet in the downstream manifold to control the counter-current flow of a desorption gas across the second adsorbent bed only.

27. An apparatus as claimed in claim 26, wherein the downstream manifold contains a first exhaust outlet for feed gas and a second exhaust outlet for second regeneration gas, the intermediate manifold contains a third exhaust outlet for desorption gas, and the upstream manifold contains a fourth exhaust outlet for first regeneration gas.

28. An apparatus as claimed in claim 26, further comprising an accumulation vessel upstream of the upstream manifold for the accumulation of liquefied feed during passing of the first and second regeneration gases and the desorption gas across the adsorbent beds.

29. An apparatus as claimed in claim 26, wherein an additional first adsorbent bed and an additional second adsorbent bed are connected to the upstream manifold, intermediate manifold and downstream manifold such that feed gas is passed across one first and second adsorbent bed while first and second regeneration gases and desorption gas are passed across the other first and second adsorbent bed, with periodic changes.

30. An apparatus for carrying out a process for recovering at least one inert gas selected from the group consisting of xenon and krypton from a liquefied feed gas containing said inert gas and one or more impurities selected from carbon dioxide, nitrous oxide and hydrocarbons, said apparatus comprising:

a first adsorbent bed containing an adsorbent for one or more of said impurities;

a second adsorbent bed downstream of the first adsorbent bed and containing a Li and Ag exchanged X-type zeolite;

a mechanism for feeding the liquefied feed gas to the first adsorbent bed;

a mechanism for vaporising liquefied gas from said first adsorbent bed prior to feeding to said second adsorbent bed; and a mechanism for feeding a desorption gas to the second adsorbent bed.

31. An apparatus as claimed in claim 30, wherein said mechanism for regenerating the first adsorbent bed comprises a mechanism for passing a regeneration gas through the bed.

32. An apparatus as claimed in claim 31, wherein said mechanism for passing a regeneration gas through the first adsorption bed does so in the counter-current direction to the flow of liquefied feed gas through the bed.

33. An apparatus as claimed in claim 30, wherein said mechanism for passing a desorption gas through the second adsorption bed does so in the counter-current direction to the flow of vaporised gas through the bed.

34. An apparatus as claimed in claim 30, further comprising a mechanism for passing an oxygen-displacing gas through the second adsorption bed in the co-current direction to the flow of the vaporised gas through the bed.

35. An apparatus as claimed in claim 30, wherein the adsorbent in the first bed is silica gel.

* * * * *